(12) United States Patent
Makino

(10) Patent No.: US 7,635,465 B2
(45) Date of Patent: Dec. 22, 2009

(54) REDUCING AGENT FOR STRAIGHTENING CURLY HAIR AND PROCESS FOR STRAIGHTENING CURLY HAIR

(75) Inventor: Yoshiyuki Makino, Osaka (JP)

(73) Assignee: Milbon Co., Ltd., Osaka-Shi (JP)

( * ) Notice: Subject to any disclaimer, the term of this patent is extended or adjusted under 35 U.S.C. 154(b) by 977 days.

(21) Appl. No.: 11/095,516

(22) Filed: Apr. 1, 2005

(65) Prior Publication Data

US 2006/0222618 A1    Oct. 5, 2006

(51) Int. Cl.
*A61Q 5/04*    (2006.01)
*A61K 8/18*    (2006.01)

(52) U.S. Cl. .................................. 424/70.2
(58) Field of Classification Search ............. 424/70.2, 424/71, 72, 76
See application file for complete search history.

(56) References Cited

U.S. PATENT DOCUMENTS 4,547,365 A * 10/1985 Kubo et al. ............ 424/70.5
5,641,809 A *  6/1997 Hagen et al. ............ 514/558
6,125,856 A  10/2000 Yamashita
6,517,822 B1 *  2/2003 Buck .................... 424/70.2

FOREIGN PATENT DOCUMENTS

JP    2002-363041    12/2002
JP    2003113050 A *  4/2003

OTHER PUBLICATIONS

Takahashi et al., Composition for providing permanent wavy hair appearance to hair, contains agent containing polychlorinated dimethyl methylene piperidinium and agent containing polyoxyethylene alkyl ether phosphoric acid, Derwent Abstract, Apr. 18, 2003, pp. 1-6.*
Zviak, Charles, "The Science of Hair Care;" *Marcel Dekker, Inc.*, pp. 207-209. (1986).

* cited by examiner

*Primary Examiner*—Johann R Richter
*Assistant Examiner*—Andriae M Holt
(74) *Attorney, Agent, or Firm*—Kratz, Quintos & Hanson, LLP

(57) ABSTRACT

The present invention aims to provide a reducing agent for straightening curly hair that can deal with various kinds of hair damage and various degrees of curling and a process for straightening curly hair, which does not cause breaking and insufficient straightening of curly hair. Specifically, the present invention relates to reducing agent for straightening curly hair comprising (A) ammonium thioglycolate and/or monoethanol amine thioglycolate, (B) at least one cysteine selected from the group consisting of L-cysteine, DL-cysteine, N-acetyl-L-cysteine, L-cysteine monohydrochloride and DL-cysteine monohydrochloride, (C) monoethanol amine and (D) ammonium hydrogen carbonate and/or ammonia; wherein the weight ratio of (C)/(D) is 1 to 15.

11 Claims, No Drawings

REDUCING AGENT FOR STRAIGHTENING CURLY HAIR AND PROCESS FOR STRAIGHTENING CURLY HAIR

BACKGROUND OF THE INVENTION

The present invention relates a reducing agent for straightening curly hair and a process for straightening curly hair.

In the U.S.A, a cold permanent waving agent having thioglycolic acid as the main component has been studied and developed from around 1940. Thioglycolic acid has been compounded to reducing agents for cold permanent waving, which reduces hair, from the viewpoints that thioglycolic acid is prepared relatively easily, is harmless in terms of health and hygiene, has little odor and maintains favorable waves. Usually, when thioglycolic acid or salts thereof are used as the active ingredient of a reducing agent for waving, high waving strength can be obtained, but the damage to hair is large. Also, when cysteine or salts thereof are used as the active ingredient, the damage to hair is small, but waving strength is weak. To solve such problems, known is a reducing agent, which has a certain waving strength and suppresses damage to the hair, by using thioglycolic acid or salts thereof and cysteine or salts thereof together as the active ingredient and adjusting the pH and alkalinity to a particular range (see JP-A-2002-363041).

However, when this reducing agent is used for straightening curly hair, depending on the curling degree, physical load such as stretching by a comb must be applied, while maintaining the hair in a straight condition under tension. Therefore, according to the above reducing agent, the hair is not sufficiently softened and there is the problem that the desired effects cannot be obtained. Also, to sufficiently soften hair, a preparation having high pH containing a large amount of an alkali agent must also be used and as a result, there is the problem that damage to hair, such as breaking at the roots and removal of cuticles, cannot be reduced.

Also, in the case of hair heavily damaged by coloring, protein in the hair has escaped, thus being more susceptible to external physical influence. As a result, when conducting straightening treatment of curly hair using a comb or a high temperature hair styling iron, the damage received is considerably larger than in the case of permanent waving treatment. In this way, satisfactory effects cannot be obtained by the conventional process for straightening curly hair, due to factors such as the thickness, the curling degree and the degree of damage of hair and the pH of the reducing agent for straightening curly hair.

In order to solve such problems, known is the process for permanently straightening, repairing and styling curly hair using a reducing agent for straightening curly hair that can be easily rinsed off (see Japanese Patent No. 3340999). However, according to this process, the hair is divided into small blocks, the first agent for straightening curly hair is applied to the hair of each block and thereafter, the hair must be wrapped in plastic wrap. Thus, the working efficiency is extremely poor and also, there is the problem that experience is necessary to conduct the process.

SUMMARY OF THE INVENTION

The present invention aims to provide a reducing agent for straightening curly hair that can deal with various kinds of hair damage and various degrees of curling and a process for straightening curly hair, which does not cause breaking and insufficient straightening of curly hair.

As a result of intensive studies to solve the above problems, a reducing agent for straightening curly hair was found to have an extremely high effect of straightening curly hair and effect of inhibiting hair damage, by containing a combination of specific thioglycolates and cysteines as the active ingredient of the reducing agent and adding a specific amount of monoethanol amine and ammonium hydrogen carbonate and/or ammonia as an alkali agent. Thus, the present invention was reached.

That is, the present invention relates to a reducing agent for straightening curly hair comprising (A) ammonium thioglycolate and/or monoethanol amine thioglycolate,
(B) at least one cysteine selected from the group consisting of L-cysteine, DL-cysteine, N-acetyl-L-cysteine, L-cysteine monohydrochloride and DL-cysteine monohydrochloride,
(C) monoethanol amine, and
(D) ammonium hydrogen carbonate and/or ammonia;

wherein the weight ratio of (C)/(D) is 1 to 15.

The amount of (A) in the reducing agent for straightening curly hair is preferably 1 to 25% by weight converted to thioglycolic acid.

In the reducing agent for straightening curly hair, (B) is preferably L-cysteine monohydrochloride.

In the reducing agent for straightening curly hair, (B) preferably contains N-acetyl-L-cysteine, L-cysteine monohydrochloride and DL-cysteine monohydrochloride and the weight ratio thereof is N-acetyl-L-cysteine:L-cysteine monohydrochloride:DL-cysteine monohydrochloride=0.1 to 5:1 to 10:1 to 10.

The amount of (D) in the reducing agent for straightening curly hair is preferably 0.1 to 10% by weight.

The reducing agent for straightening curly hair preferably contains shea butter.

The amount of the shea butter in the reducing agent for straightening curly hair is preferably 0.05 to 10% by weight.

The reducing agent for straightening curly hair preferably contains lanolin fatty acid ester.

The lanolin fatty acid ester is preferably cholesteryl lanolate and the amount thereof is 0.1 to 10% by weight.

The present invention also relates to a process for straightening curly hair, which comprises (1) the step of washing hair with water, applying a scalp protecting agent to the scalp and thereafter, applying a root softening agent near the hair roots;
(2) the step of applying the above reducing agent for straightening curly hair to the hair and leaving for 5 to 30 minutes;
(3) the step of subjecting hair to a softening test, washing with water and thereafter drying;
(4) the step of applying an oxidizing agent for straightening curly hair containing an oxidant to hair and leaving for 5 to 15 minutes; and
(5) the step of washing with water and drying the hair.

The scalp protecting agent in the process for straightening curly hair is preferably a non-aqueous preparation comprising hydrocarbon, vegetable oil and silicone oil.

The root softening agent in the process for straightening curly hair preferably contains cysteine and/or sulfite salt.

The present invention also relates to a process for straightening curly hair, which comprises (a) the step of washing hair with water, applying a scalp protecting agent to the scalp and thereafter, applying a root softening agent near the hair roots;
(b) the step of applying the above reducing agent for straightening curly hair to the hair and leaving for 5 to 30 minutes;
(c) the step of subjecting hair to a softening test, washing with water and thereafter drying; and (d) the step of conducting straightening treatment of curly hair using a high temperature hair styling iron having a surface temperature of 60 to 220° C.; and (e) the step of applying an oxidizing agent for straightening curly hair containing an oxidant to hair and leaving for 5 to 15 minutes.

In the process for straightening curly hair, after the reducing agent for straightening curly hair is washed off with water in step (c), a conditioning agent is preferably applied.

In the process for straightening curly hair, the conditioning agent preferably contains at least one compound selected from the group consisting of polyether modified silicone, polyol and lanolin fatty acid aminopropylethyl dimethyl ammonium ethylsulfate.

DETAILED DESCRIPTION

The present invention relates to a reducing agent for straightening curly hair comprising (A) ammonium thioglycolate and/or monoethanol amine thioglycolate, (B) at least one cysteine selected from the group consisting of L-cysteine, DL-cysteine, N-acetyl-L-cysteine, L-cysteine monohydrochloride and DL-cysteine monohydrochloride, (C) monoethanol amine, and (D) ammonium hydrogen carbonate and/or ammonia; wherein the weight ratio of (C)/(D) is 1 to 15.

In the reducing agent for straightening curly hair of the present invention, (A) is ammonium thioglycolate and/or monoethanol amine thioglycolate. The amount thereof is preferably 1 to 25% by weight, more preferably 5 to 20% by weight converted to thioglycolic acid. When the amount is more than 25% by weight, the ammonium thioglycolate and/or monoethanol amine thioglycolate tend to act on the hair and scalp more than necessary and as a result, damage to the hair and irritation to the scalp tend to occur. When the amount is less than 1% by weight, the straightening effect tends to be insufficient.

In the reducing agent of the present invention, (B) is at least one cysteine selected from the group consisting of L-cysteine, DL-cysteine, N-acetyl-L-cysteine, L-cysteine monohydrochloride and DL-cysteine monohydrochloride, preferably L-cysteine monohydrochloride. According these cysteines, the cuticle, which is located on the outermost layer of hair, is softened sufficiently and a constant straightening effect can be obtained for various kinds of curly hair. (B) preferably contains N-acetyl-L-cysteine, L-cysteine monohydrochloride and DL-cysteine monohydrochloride and the weight ratio thereof is N-acetyl-L-cysteine:L-cysteine monohydrochloride:DL-cysteine monohydrochloride=0.1 to 5:1 to 10:1 to 10. The amount of the cysteine is preferably 0.1 to 10% by weight, more preferably 0.1 to 5% by weight. When the amount is more than 10% by weight, an unpleasant odor becomes strong and damage to the hair and irritation to the scalp tend to occur. When the amount is less than 0.1% by weight, the straightening effect tends to be insufficient.

The swelling degree of hair increases along with increase in pH and therefore, it is known that a reducing composition having higher pH exhibits a stronger straightening effect. In the reducing agent of the present invention, the alkali agent is (C) monoethanol amine and (D) ammonium hydrogen carbonate and/or ammonia and the weight ratio of (C)/(D) is 1 to 15, preferably 1 to 10. When the weight ratio of (C)/(D) is lower than 1, the pungent odor of ammonia tends to become strong. When the weight ratio is higher than 15, the hair cannot be sufficiently swelled and as a result, the reducing agent cannot permeate into the hair and the desired straightening effect may not be obtained. The total amount of (C) and (D) is preferably 1 to 10% by weight. When the total amount is more than 10% by weight, the hair is swelled excessively, tending to cause damage to the hair surface. When the total amount is less than 1% by weight, the hair cannot be sufficiently swelled and as a result, the reducing agent cannot permeate into the hair and the desired straightening effect may not be obtained.

The reducing agent for straightening curly hair of the present invention preferably contains shea butter, to obtain the effect of significantly improving touch such as moist feel. The amount of the shea butter is preferably 0.05 to 10% by weight, more preferably 1 to 5% by weight. When the amount is more than 10% by weight, the hair tends to feel excessively sticky when the reducing agent for straightening curly hair is washed off with water. When the amount is less than 0.05% by weight, moist feel may not be obtained when finished.

The reducing agent for straightening curly hair of the present invention preferably contains lanolin fatty acid ester. By adding the lanolin fatty acid ester, the effects of the shea butter are enhanced. Examples of the lanolin fatty acid ester are lauryl lanolate, stearyl lanolate, behenyl lanolate, octyl dodecyl lanolate and cholesteryl lanolate and cholesteryl lanolate is preferable. The amount of the lanolin fatty acid ester is preferably 0.1 to 5% by weight, more preferably 0.1 to 1% by weight. When the amount is more than 5% by weight, the hair tends to feel excessively sticky when the reducing agent for straightening curly hair is washed off with water. When the amount is less than 0.1% by weight, moist feel may not be obtained when finished.

When preparing the reducing agent for straightening curly hair of the present invention, besides the above essential components, any component that is usually compounded in cosmetics can be added accordingly, as long as the effects of the present invention are not lost. Examples of such components are cationic surfactants, nonionic surfactants, anionic surfactants, ampholytic surfactants, fats and oils, higher fatty acids, higher alcohols, esters, lubricants, antiseptics, chelating agents, perfumes and colorants.

These optional components are not particularly limited. Suitable examples of the cationic surfactant are lanolin fatty acid aminopropylethyl dimethyl ammonium ethylsulfate, alkyl trimethyl ammonium chloride, dialkyl dimethyl ammonium chloride (the number of carbon atoms of the alkyl group is preferably 14 to 18), distearyl dimethyl ammonium chloride, lauryl trimethyl ammonium chloride, stearyl trimethyl ammonium chloride, stearyl dimethyl benzyl ammonium chloride, cetyl trimethyl ammonium bromide, stearyl trimethyl ammonium bromide, benzalkonium chloride, benzetonium chloride and diethyl aminoethyl amide stearate. Suitable examples of the nonionic surfactant are polyoxyethylene cetyl ether, polyoxyethylene oleyl ether, polyoxyethylene hydrogenated castor oil, alkyl glycoxide, sucrose fatty acid ester, sorbitan fatty acid ester, polyoxyethylene polyoxypropylene glycol, polyglycerine fatty acid ester, palm oil fatty acid diethanol amide, diethanol amide laurate and sorbitan monostearate. Suitable examples of the anionic surfactant are N-acyl-L-glutamic acid triethanol amine, N-acyl-L-glutamic acid sodium, sodium alkylsulfate, sodium laurylsulfate, sodium polyoxyethylene laurylethersulfate, sodium α-oleate, sodium tetradecene sulfonate, triethanolamine dodecylbenzenesulfonate, polyoxyethylene laurylpetherphosphate and polyoxyethylene oleyletherphosphate. Suitable examples of the ampholytic surfactant are 2-alkyl-N-carboxymethyl-N-hydroxyethyl imidazolinium betaine, sodium β-laurylaminopropionate and lauryldimethyl aminoacetic acid betaine.

Suitable examples of the fat and oil are avocado oil, almond oil, olive oil, grapeseed oil, rice bran oil, shea butter, soyabean oil, camelia oil, castor oil, sunflower seed oil, macadamia nut oil, meadow form seed oil, palm oil, hydrogenated oil and vitelline oil.

Suitable examples of the higher fatty acid are isostearic acid, oleic acid, stearic acid, palmitic acid, behenic acid, myristic acid, lauric acid, lanolin fatty acid and linoleic acid.

Suitable examples of the higher alcohol are isostearyl alcohol, oleyl alcohol, glyceryl monocetyl ether, cholesterol, stearyl alcohol, cetanol, cetostearyl alcohol, batyl alcohol, behenyl alcohol, lauryl alcohol and lanolin alcohol.

Suitable examples of the esters are isostearyl glycerylether, isocetyl isostearate, glyceryl isostearate, cetyl 2-ethylhexanoate, octyldodecyl oleate, cetyl lactate, cetyl palimitate, isopropyl myristate, myristyl myristate and diisostearyl malate.

Suitable examples of the lubricant are glycerin, polyethylene glycol, propylene glycol, dipropylene glycol, 1,3-butylene glycol, sorbitol, maltitol and pyrrolidone carboxylic acid.

Suitable examples of the antiseptic are methyl paraoxybenzoate, propyl paraoxybenzoate, sodium benzoate and phenoxy ethanol.

Suitable examples of the chelating agent are ethylenediaminetetraacetic acid or salts thereof, diethylenetriaminepentaacetic acid or salts thereof, hydroxyethylethylenediaminetriacetic acid or salts thereof and hydroxyethane diphosphonic acid or salts thereof.

The form of the reducing agent for straightening curly hair of the present invention is not particularly limited and various forms can be employed such as cream, lotion, gel, foam and spray.

The process for straightening curly hair of the present invention is described below. The steps of the process for straightening curly hair of the present invention can be adjusted accordingly within the range of the knowledge of one skilled in the art.

The present invention relates to a process for straightening curly hair, which comprises (1) the step of washing hair with water, applying a scalp protecting agent to the scalp and thereafter, applying a root softening agent near the hair roots; (2) the step of applying the above reducing agent for straightening curly hair to the hair and leaving for 5 to 30 minutes; (3) the step of subjecting hair to a softening test, washing with water and thereafter drying; (4) the step of applying an oxidizing agent for straightening curly hair containing an oxidant to hair and leaving for 5 to 15 minutes; and (5) the step of washing with water and drying the hair. Because the reducing agent for straightening curly hair of the present invention does not easily dry when applied to hair and therefore can be left as it is without using plastic wrap, the process for straightening curly hair is simple.

The scalp protecting agent in step (1) is not particularly limited as long as the agent prevents the preparation for straightening curly hair from directly touching the scalp. From the viewpoint of definitely protecting the scalp, not inhibiting the effects of the reducing agent for straightening curly hair used in the present invention, workability when preparing and handling properties when using, a non-aqueous preparation comprising hydrocarbon, vegetable oil and silicone oil, which is liquid at room temperature, is preferable. The amount of the scalp protecting agent that is applied is not particularly limited and preferably, 4 to 7 g is applied. When the amount is less than 4 g, the scalp may not be protected sufficiently and when the amount is more than 7 g, the scalp protecting agent is difficult to rinse off and the roots of the hair tend to become rough and sticky.

Examples of the hydrocarbon are liquid paraffin, light liquid isoparaffin, squalane and α-olefin oligomer and at least one of these hydrocarbons can be compounded. The amount of the hydrocarbon is preferably 20 to 80% by weight, more preferably 30 to 60% by weight. When the amount is more than 80% by weight, the scalp protecting agent is difficult to rinse off and the roots of the hair tend to become rough and sticky. When the amount is less than 20% by weight, the effect of protecting the scalp may not be obtained.

Examples of the vegetable oil are avocado oil, almond oil, sesame oil, soyabean oil, camelia oil, jojoba oil, macadamia nut oil and eucalyptus oil and at least one of these vegetable oils can be compounded. The amount is the vegetable oil is preferably 0.5 to 10% by weight, more preferably 1 to 5% by weight. When the amount is more than 10% by weight, the scalp protecting agent is difficult to rinse off and the roots of the hair tend to become rough and sticky. When the amount is less than 0.5% by weight, not only is the scalp unprotected, but also, the touch of the hair surface tends to become poor.

Examples of the silicone oil are dimethyl silicone, high polymerization degree dimethyl silicone, cyclic silicone, polyether modified silicone and amino modified silicone and at least one of these silicone oils can be compounded. The amount of the silicone oil is preferably 10 to 85% by weight, more preferably 40 to 60% by weight. When the amount is more than 85% by weight, the scalp protecting agent is difficult to rinse off and the roots of the hair tend to become rough and sticky. When the amount is less than 10% by weight, not only is the scalp unprotected, but also, the touch of the hair surface tends to become poor.

When preparing the scalp protecting agent used in the present invention, besides the other components, components that are usually compounded in cosmetics can be added accordingly as long as the effects of the present invention are not lost. Also, the form of the scalp protecting agent is not particularly limited.

The root softening agent used in step (1) is not particularly limited as long the agent can soften the roots of hair a little. From the viewpoint of preventing breaking of the roots by softening, workability when preparing and handling properties when using, cysteine and/or sulfite salt, which are reducing agents having weak reducing power, are preferably compounded. Examples of cysteine are cysteine hydrochloride and N-acetyl-Lcysteine and examples of the sulfite salt are bisulfite and pyrosulfite. The root softening agent is preferably applied to the area 1 to 1.5 cm from the hair roots in an amount of 30 to 70 ml.

When preparing the root softening agent of the present invention, components that are usually compounded in cosmetics can be added accordingly as long as the effects of the present invention are not lost. Also, the form of the root softening agent is not particularly limited.

The amount of the reducing agent for straightening curly hair of the present invention that is applied to the hair is not particularly limited and preferably, 200 to 250 ml is applied to shoulder-length hair. When the amount is less than 200 ml, a long period of time tends to be necessary to sufficiently soften the hair and when the amount is more than 250 ml, more of the reducing agent than necessary is used, thus being economically unfavorable. After application, the reducing agent is preferably left for 5 to 30 minutes, more preferably 20 to 30 minutes. When left for less than 5 minutes, the hair may not be sufficiently softened and when left for more than 30 minutes, the hair tends to be damaged.

In the "softening test" of step (3), the three tests of "tensile test", "knot test" and "combing test" are conducted. The "tensile test" and the "knot test" are conducted to the part where the reducing agent for straightening curly hair was first applied immediately after application. This is so that the condition before and after application can be observed. The "tensile test" is conducted by holding one strand of hair at the root and the end and then pulling and this test confirms that the optimally softened state is when the hair is flexibly stretched within the range of 30 to 50%. The "knot test" is conducted by wiping off the preparation from the hair with a wet towel, forming a small ring of a 5 to 10 mm diameter at the root, middle and end of the hair, loosely tying the knot until the knot ring tightens and laying the knot on the palm of a hand. This test confirms that the hair is sufficiently softened when the knot is still tied when released. The "combing test" is conducted by combing directly downward from the hair roots using a comb having rough teeth so that tension is not applied. This test confirms that the hair is sufficiently softened when the curly areas remain stretched.

The oxidizing agent for straightening curly hair used in step (4) is not particularly limited. From the viewpoint that the S—S bonds in the hair that are broken by the reducing agent for straightening curly hair are rebonded by oxidization, examples of the oxidant are oxidizing agents such as hydrogen peroxide solution, sodium bromate and sodium perborate and from the viewpoint of strong oxidization force, hydrogen peroxide solution is preferably compounded. To the oxidizing agent, for example, a pH buffer, a thickener and a surfactant can be added. The oxidizing agent for straightening curly hair is preferably applied in an amount of 200 to 250 ml to shoulder-length hair and after application, is preferably left to dry for 5 to 15 minutes. When left for less than 5 minutes, oxidization tends to be insufficient and when the left for more than 15 minutes, the hair tends to be damaged.

The present invention also relates to a process for straightening curly hair, which comprises (a) the step of washing hair with water, applying a scalp protecting agent to the scalp and thereafter, applying a root softening agent near the hair roots; (b) the step of applying the above reducing agent for straightening curly hair to the hair and leaving for 5 to 30 minutes; (c) the step of subjecting the hair to a softening test, washing with water and thereafter drying, (d) the step of conducting straightening treatment of curly hair using a high temperature hair styling iron having a surface temperature of 60 to 220° C. and (e) the step of applying an oxidizing agent for straightening curly hair containing an oxidant to hair and leaving for 5 to 15 minutes In the process for straightening curly hair using a high temperature hair styling iron, application of the scalp protecting agent to the scalp and the root softening agent near the hair roots in step (a), application of the reducing agent for straightening curly hair to the hair in step (b) and the softening test of step (c) are conducted in the process described above. Also, in step (c), after the reducing agent for straightening curly hair is washed off with water, 10 to 20 g of a conditioning agent is preferably applied to shoulder-length hair before drying.

The high temperature hair styling iron is not particularly limited as long as the surface temperature of the iron can be heated to 60 to 220° C. and straightening treatment of curly hair can be conducted. From the viewpoint of operational efficiency, Thermal Effect Iron CR, Thermal Effect Iron FS and Thermal Effect G Short (all available from Milbon Co., Ltd.) are preferable. The straightening treatment of curly hair can be conducted by taking a 1.2 cm width slice of hair at the nape, straightening the surface with a comb while applying tension and pressing for about 3 seconds using the high temperature hair styling iron. The surface temperature of the high temperature hair styling iron is preferably 60 to 220° C., more preferably 160 to 200° C.

When preparing the conditioning agent used in the present invention, preferably at least one of polyether modified silicone, polyol and lanolin fatty acid aminopropylethyl dimethyl ammonium ethylsulfate is added. Examples of the polyether modified silicone are polyoxyethylene-methylpolysiloxane copolymer and poly(oxyethyleneoxypropylene)methylpolysiloxane copolymer, examples of the polyol are ethylene glycol, propylene glycol, isoprene glycol, 1,3-butyleneglycol, glycerin and polyethyleneglycol. Also, the form of the conditioning agent is not particularly limited.

Hereinafter, the present invention is explained in detail by means of Examples, but the present invention is not limited thereto. In the following Examples, "%" showing the concentration of the components represents "% by weight".

EXAMPLES 1 TO 15 AND COMPARATIVE EXAMPLES 1 TO 9

The reducing agents for straightening curly hair of Examples 1 to 15 and Comparative Examples 1 to 9 were prepared according to the composition shown in Tables 1 to 3. The reducing agents were prepared by mixing each of the compounds according to the usual method. The oxidizing agent for straightening curly hair and the conditioning agent, which are used together with the scalp protecting agent, the root softening agent and the reducing agent for straightening curly hair described above, were prepared according to the composition shown in Tables 4 to 7 in the same manner as the reducing agent for straightening curly hair.

TABLE 1

|  | Com. Ex. | | | | | | | | |
| --- | --- | --- | --- | --- | --- | --- | --- | --- | --- |
|  | 1 | 2 | 3 | 4 | 5 | 6 | 7 | 8 | 9 |
| Ammonium thioglycolate (A) | — | 2.0 | 2.0 | 2.0 | — | 10.0 | — | 2.0 | — |
| Monoethanol amine thioglycolate (A) | — | — | — | — | 3.0 | — | 15.0 | 6.0 | — |
| N-acetyl-L-cysteine (B) | — | — | — | — | — | — | — | — | 0.4 |
| L-cysteine hydrochloride (B) | 2.0 | — | 2.0 | 2.0 | — | — | — | — | 0.8 |
| DL-cysteine hydrochloride (B) | — | — | — | — | — | — | — | — | 0.8 |
| Monoethanol amine (C) | 3.0 | 3.0 | — | 3.0 | 3.0 | 3.0 | 3.0 | 3.0 | 3.0 |
| Ammonium hydrogen carbonate (D) | 1.0 | 1.0 | 1.0 | — | 1.0 | 1.0 | 1.0 | 1.0 | 1.0 |
| Ammonia water (25%) (D) | 1.0 | 1.0 | 1.0 | — | 1.0 | 1.0 | 1.0 | 1.0 | 1.0 |
| Shea butter (E) | — | — | — | — | — | — | — | — | — |
| Cholesteryl lanolate (F) | — | — | — | — | — | — | — | — | — |
| Stearyl alcohol | 1.0 | 1.0 | 1.0 | 1.0 | 1.0 | 1.0 | 1.0 | 1.0 | 1.0 |
| Polyoxyethylene oleyletherphosphate | 0.5 | 0.5 | 0.5 | 0.5 | 0.5 | 0.5 | 0.5 | 0.5 | 0.5 |
| Sorbitan monostearate | 1.0 | 1.0 | 1.0 | 1.0 | 1.0 | 1.0 | 1.0 | 1.0 | 1.0 |

TABLE 1-continued

| | Com. Ex. | | | | | | | | |
|---|---|---|---|---|---|---|---|---|---|
| | 1 | 2 | 3 | 4 | 5 | 6 | 7 | 8 | 9 |
| Perfume | 0.3 | 0.3 | 0.3 | 0.3 | 0.3 | 0.3 | 0.3 | 0.3 | 0.3 |
| Total amount is adjusted to 100 with purified water | variable | variable | variable | variable | variable | variable | variable | variable | variable |
| pH | 9.3 | 9.3 | 9.0 | 9.1 | 9.3 | 9.3 | 9.3 | 9.3 | 9.3 |

TABLE 2

| | Ex. | | | | | | | | |
|---|---|---|---|---|---|---|---|---|---|
| | 1 | 2 | 3 | 4 | 5 | 6 | 7 | 8 | 9 |
| Ammonium thioglycolate (A) | 2.0 | 2.0 | 10.0 | — | 2.0 | 2.0 | 2.0 | 2.0 | 2.0 |
| Monoethanol amine thioglycolate (A) | — | — | — | 15.0 | 6.0 | — | 6.0 | 6.0 | — |
| N-acetyl-L-cysteine (B) | — | — | — | — | — | 0.4 | — | — | 0.4 |
| L-cysteine hydrochloride (B) | 2.0 | 2.0 | 2.0 | 2.0 | 2.0 | 0.8 | 2.0 | 2.0 | 0.8 |
| DL-cysteine hydrochloride (B) | — | — | — | — | — | 0.8 | — | — | 0.8 |
| Monoethanol amine (C) | 3.0 | 3.0 | 3.0 | 3.0 | 3.0 | 3.0 | 1.0 | 10.0 | 3.0 |
| Ammonium hydrogen carbonate (D) | 1.0 | — | — | — | 1.0 | 1.0 | 1.0 | 1.0 | — |
| Ammonia water (25%) (D) | 1.0 | 1.0 | 1.0 | 1.0 | 1.0 | 1.0 | 1.0 | 1.0 | 1.0 |
| Shea butter (E) | — | — | — | — | — | — | — | — | 1.5 |
| Cholesteryl lanolate (F) | — | — | — | — | — | — | — | — | — |
| Stearyl alcohol | 1.0 | 1.0 | 1.0 | 1.0 | 1.0 | 1.0 | 1.0 | 1.0 | 1.0 |
| Polyoxyethylene oleyletherphosphate | 0.5 | 0.5 | 0.5 | 0.5 | 0.5 | 0.5 | 0.5 | 0.5 | 0.5 |
| Sorbitan monostearate | 1.0 | 1.0 | 1.0 | 1.0 | 1.0 | 1.0 | 1.0 | 1.0 | 1.0 |
| Perfume | 0.3 | 0.3 | 0.3 | 0.3 | 0.3 | 0.3 | 0.3 | 0.3 | 0.3 |
| Total amount is adjusted to 100 with purified water | variable | variable | variable | variable | variable | variable | variable | variable | variable |
| pH | 9.3 | 9.3 | 9.3 | 9.3 | 9.3 | 9.3 | 8.9 | 9.4 | 9.3 |

TABLE 3

| | Ex. | | | | | |
|---|---|---|---|---|---|---|
| | 10 | 11 | 12 | 13 | 14 | 15 |
| Ammonium thioglycolate (A) | 2.0 | 2.0 | 2.0 | 2.0 | 2.0 | 2.0 |
| Monoethanol amine thioglycolate (A) | — | — | — | — | 6.0 | — |
| N-acetyl-L-cysteine (B) | 0.4 | — | 0.4 | 0.4 | — | 4.0 |
| L-cysteine hydrochloride (B) | 0.8 | 8.0 | 0.8 | 0.8 | 2.0 | 8.0 |
| DL-cysteine hydrochloride (B) | 0.8 | — | 0.8 | 0.8 | — | 8.0 |
| Monoethanol amine (C) | 3.0 | 3.0 | 3.0 | 3.0 | 3.0 | 3.0 |
| Ammonium hydrogen carbonate (D) | — | — | — | — | 0.3 | 1.0 |
| Ammonia water (25%) (D) | 1.0 | 1.0 | 1.0 | 1.0 | — | 1.0 |
| Shea butter (E) | 1.5 | — | 5.0 | 5.0 | — | — |
| Cholesteryl lanolate (F) | 0.2 | — | — | 2.0 | — | — |
| Stearyl alcohol | 1.0 | 1.0 | 1.0 | 1.0 | 1.0 | 1.0 |
| Polyoxyethylene oleyletherphosphate | 0.5 | 0.5 | 0.5 | 0.5 | 0.5 | 0.5 |
| Sorbitan monostearate | 1.0 | 1.0 | 1.0 | 1.0 | 1.0 | 1.0 |
| Perfume | 0.3 | 0.3 | 0.3 | 0.3 | 0.3 | 0.3 |
| Total amount is adjusted to 100 with purified water | variable | variable | variable | variable | variable | variable |
| pH | 9.3 | 9.3 | 9.3 | 9.3 | 9.0 | 9.3 |

TABLE 4

| Raw material | Amount |
|---|---|
| Hydrogen peroxide solution (35%) | 3.0 |
| Disodium hydrogen phosphate | 1.0 |
| Dipropylene glycol | 2.0 |
| Ammonium acryloyl dimethyl taurate/vinylpyrrolidone copolymer | 0.5 |
| Polyoxyethylene lauryl ether | 0.5 |
| Liquid paraffin | 2.0 |
| pH (in phosphoric acid) | 3.0 |
| Total amount is adjusted to 100 with purified water | variable |

TABLE 5

| Raw material | Amount |
|---|---|
| Light liquid paraffin | 40.0 |
| Squalane | 3.0 |
| Macadamia nut | 2.0 |
| Decamethyl cyclopentane siloxane | 40.0 |
| High polymerization methyl polysiloxane | 15.0 |

TABLE 6

| Raw material | Amount |
| --- | --- |
| Anhydrous sodium sulfite | 1.0 |
| Cetostearyl alcohol | 5.0 |
| Polyoxyethylene cetyl ether | 4.0 |
| 1,3-butyleneglycol | 1.0 |
| Total amount is adjusted to 100 with purified water | variable |

TABLE 7

| Raw material | Amount |
| --- | --- |
| Polyoxyethylene polyoxypropylene butyl ether | 0.5 |
| Polyoxyethylene hydrogenated castor oil (40 E.O.) | 1.0 |
| Diethoxyethyl succinate | 0.5 |
| Polyoxyethylene•methyl polysiloxane copolymer | 0.1 |
| Polyethylene glycol | 2.0 |
| Hydrolyzed keratin | 0.1 |
| Ethanol | 5.0 |
| Perfume | 0.1 |
| Total amount is adjusted to 100 with purified water | variable |

For the curly hair used for straightening treatment, curly hair of a strong curling degree was used. While adjusting the curling degree of the hair as uniform as possible, a bundle of hair having length of 12 cm (measured in the natural condition without stretching) and weight of 0.5 g was prepared. After washing in a washing solution adjusted to 5 w/v % polyoxyethylene (9) lauryl ether, 20 ml MEDTA and pH 4.5, the bundle was thoroughly washed with distilled water and air-dried to obtain the test sample.

Subsequently, the reducing agents for straightening curly hair of Examples 1 to 15 and Comparative Examples 1 to 9 were respectively applied to the above bundles in an amount of 1 ml and after leaving for 15 minutes at 25° C., the bundles were thoroughly washed with water and air-dried. Thereafter, the oxidizing agents for straightening curly hair were respectively applied to each bundle in an amount of 1 ml and after leaving for 10 minutes at 25° C., the bundles were thoroughly washed with water and air-dried to complete the straightening treatment of curly hair.

The bundles subjected to the above treatment were measured for the straightening ratio and the tensile strength of the hair. The measurement methods and evaluation results are described below.

(Straightening Ratio)

One end of the treated bundle was fixed to and hung from a panel and the entire length was measured. The straightening ratio was found from the following equation.

Straightening ratio=$(A-B)/(C-B) \times 100$

A: Total length of bundle after straightening treatment (mm)
B: Total length of bundle before straightening treatment in normal state (mm)
C: Total length of bundle before straightening treatment in stretched state (mm)

(Tensile Strength)

The tensile test was conducted by taking one strand of hair from the treated bundle, fixing the hair at both sides of the area 5 cm and 6 cm from the end of the hair with glass fiber-containing tape of 1 cm width, creating the condition in which the hair may break in the area between 5 cm and 6 cm from the end of the hair and measuring the major axis and the minor axis of the hair using a micrometer. After immersing this sample for one night and one day in distilled water, the weight at break was measured using a rheometer. The tensile strength of the hair was found from the following equation and the average value of ten times was considered to be the measured value for each hair subjected to straightening treatment.

Tensile strength=$D \times 4/(E \times F \times \pi)$

D: weight at break (g)
E: major axis of hair (μm)
F minor axis of hair (μm)

(Touch Test)

The touch test was conducted for hair subjected to straightening treatment by 20 specialized panelists and the moist feel was evaluated on a scale of 5.

The evaluation criteria were as follows.

5: very good
4: good
3: normal
2: poor
1: very poor

The rating given by each panelist with respect to moist feel was added up and each hair styling composition was evaluated from the total according to the following.

The evaluation criteria were as follows.

◎: total of 80 or more
○: total of 60 to 80
Δ: total of 40 to 60
×: total of less than 40

Evaluation of ◎ and ○ were considered acceptable.

TABLE 8

| | Com. Ex. | | | | | | | | | Ex. | | |
| --- | --- | --- | --- | --- | --- | --- | --- | --- | --- | --- | --- | --- |
| | 1 | 2 | 3 | 4 | 5 | 6 | 7 | 8 | 9 | 1 | 2 | 3 |
| Straightening ratio (%) | 13 | 22 | 25 | 28 | 32 | 76 | 87 | 64 | 11 | 31 | 25 | 79 |
| Tensile strength ($\times 10^{-3}$) | 14.0 | 12.1 | 11.3 | 10.2 | 9.8 | 8.2 | 7.7 | 8.9 | 14.2 | 13.9 | 14.4 | 13.2 |
| Moist feel | ○ | Δ | Δ | Δ | Δ | X | X | X | ○ | ○ | ○ | Δ |

| | Ex. | | | | | | | | | | | |
| --- | --- | --- | --- | --- | --- | --- | --- | --- | --- | --- | --- | --- |
| | 4 | 5 | 6 | 7 | 8 | 9 | 10 | 11 | 12 | 13 | 14 | 15 |
| Straightening ratio (%) | 91 | 69 | 27 | 67 | 85 | 22 | 23 | 37 | 21 | 22 | 64 | 51 |
| Tensile strength ($\times 10^{-3}$) | 12.7 | 14.0 | 15.1 | 14.0 | 13.2 | 15.8 | 15.5 | 13.7 | 14.9 | 14.9 | 13.7 | 14.2 |
| Moist feel | Δ | Δ | ○ | Δ | Δ | ◎ | ◎ | ○ | ◎ | ◎ | Δ | ○ |

(Straightening Ratio)

As shown in Table 8, even when treated with the oxidizing agent for straightening curly hair or treated using a high temperature hair styling iron, Examples 1 to 15 all have higher values than Comparative Examples 1 to 9 and the reducing agent for straightening curly hair used in Examples exhibits an extremely excellent straightening effect.

(Tensile Strength)

As shown in Table 8, in the tensile test, even when treated with the oxidizing agent for straightening curly hair or treated using a high temperature hair styling iron, Examples 1 to 15 all have higher values than Comparative Examples 1 to 9 and the reducing agent for straightening curly hair used in Examples exhibits little damage to hair by the straightening treatment.

(Touch Test)

As shown in Table 8, while the reducing agent for straightening curly hair used in Examples 1 to 15 are all acceptable, those of Comparative Examples 1 to 9 are all unacceptable. In this way, the reducing agent for straightening curly hair of the present invention imparts moist feel to hair subjected to the straightening treatment.

According to the reducing agent for straightening curly hair of the present invention, by containing a specific amount of monoethanol amine and ammonium hydrogen carbonate and/or ammonia as an alkali agent in a reducing agent of specific thioglycolates and cysteines, an extremely high effect of straightening curly hair and effect of inhibiting hair damage can be obtained. Also, by adding shea butter and lanolin derivatives to the reducing agent for straightening curly hair, a moist feel is imparted to the hair after straightening. Furthermore, because the reducing agent for straightening curly hair has does not easily dry after being applied to the hair, the process for straightening treatment of curly hair is simple.

What is claimed is:

1. A reducing agent for straightening curly hair comprising
   (A) ammonium thioglycolate and/or monoethanol amine thioglycolate,
   (B) at least one cysteine selected from the group consisting of L-cysteine, DL-cysteine, N-acetyl-L-cysteine, L-cysteine monohydrochloride and DL-cysteine monohydrochloride,
   (C) monoethanol amine,
   (D) ammonium hydrogen carbonate and/or ammonia, wherein the weight ratio of (C)/(D) is 1 to 15,
   (E) shea butter, wherein the amount of said shea butter is 1.5 to 5.0% by weight, and
   (F) cholesteryl lanolate, wherein the amount of the cholesteryl lanolate is 0.2 to 2.0% by weight.

2. The reducing agent for straightening curly hair of claim 1, wherein the amount of (A) is 1 to 25% by weight converted to thioglycolic acid.

3. The reducing agent for straightening curly hair of claim 1, wherein (B) is L-cysteine monohydrochloride.

4. The reducing agent for straightening curly hair of claim 1, wherein (B) contains N-acetyl-L-cysteine, L-cysteine monohydrochloride and DL-cysteine monohydrochloride and the weight ratio thereof is N-acetyl-L-cysteine:L-cysteine monohydrochloride:DL-cysteine monohydrochloride=0.1 to 5:1 to 10:1 to 10.

5. The reducing agent for straightening curly hair of claim 1, wherein the amount of (D) is 0.1 to 10% by weight.

6. A process for straightening curly hair, which comprises
   (1) the step of washing hair with water, applying a scalp protecting agent to the scalp and thereafter, applying a root softening agent near the hair roots;
   (2) the step of applying the reducing agent for straightening curly hair of claim 1, to the hair and leaving for 5 to 30 minutes;
   (3) the step of subjecting hair to a softening test, washing with water and thereafter drying;
   (4) the step of applying an oxidizing agent for straightening curly hair containing an oxidant to hair and leaving for 5 to 15 minutes; and
   (5) the step of washing with water and drying the hair.

7. The process for straightening curly hair of claim 6, wherein said scalp protecting agent is a non-aqueous preparation comprising hydrocarbon, vegetable oil and silicone oil.

8. The process for straightening curly hair of claim 6, wherein said root softening agent contains cysteine and/or sulfite salt.

9. A process for straightening curly hair, which comprises
   (a) the step of washing hair with water, applying a scalp protecting agent to the scalp and thereafter, applying a root softening agent near the hair roots;
   (b) the step of applying the reducing agent for straightening curly hair of claim 1, to hair and leaving for 5 to 30 minutes;
   (c) the step of subjecting hair to a softening test, washing with water and thereafter drying; and
   (d) the step of conducting straightening treatment of curly hair using a high temperature hair styling iron having a surface temperature of 60 to 220° C.; and
   (e) the step of applying an oxidizing agent for straightening curly hair containing an oxidant to hair and leaving for 5 to 15 minutes.

10. The process for straightening curly hair of claim 9, wherein after said reducing agent for straightening curly hair is washed off with water in step (c), a conditioning agent is applied.

11. The process for straightening curly hair of claim 10, wherein said conditioning agent contains at least one compound selected from the group consisting of polyether modified silicone, polyol and lanolin fatty acid aminopropylethyl dimethyl ammonium ethylsulfate.

* * * * *